(12) United States Patent
Bonnert

(10) Patent No.: US 6,949,643 B2
(45) Date of Patent: Sep. 27, 2005

(54) THIAZOLOPYTIMIDINES AND THEIR USE AS MODULATORS OF CHEMOKINE RECEPTOR ACTIVITY

(75) Inventor: Roger Bonnert, Charnwood (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 10/474,610

(22) PCT Filed: Apr. 12, 2002

(86) PCT No.: PCT/SE02/00731

§ 371 (c)(1),
(2), (4) Date: Oct. 9, 2003

(87) PCT Pub. No.: WO02/083693

PCT Pub. Date: Oct. 24, 2002

(65) Prior Publication Data

US 2004/0157853 A1 Aug. 12, 2004

(30) Foreign Application Priority Data

Apr. 12, 2001 (SE) .............................. 0101322

(51) Int. Cl.[7] .................. C07D 513/04; C07D 475/06; C07D 471/04; A61K 31/519; A61P 11/00

(52) U.S. Cl. ...................... 544/255; 544/258; 544/286; 514/259

(58) Field of Search ................................ 544/255, 258, 544/286; 514/259

(56) References Cited

U.S. PATENT DOCUMENTS

| | | | |
|---|---|---|---|
| 3,318,900 | A | 5/1967 | Janssen |
| 4,126,689 | A | 11/1978 | Sanczuk et al. |
| 4,278,677 | A | 7/1981 | Nedelec et al. |
| 4,410,528 | A | 10/1983 | Teranishi et al. |
| 5,521,197 | A | 5/1996 | Audia |
| 6,172,067 | B1 | 1/2001 | Ito et al. |
| 6,248,755 | B1 | 6/2001 | Chapman et al. |
| 6,329,381 | B1 | 12/2001 | Kurimoto et al. |
| 6,407,121 | B1 | 6/2002 | Nagamine et al. |
| 6,432,981 | B1 | 8/2002 | Finke et al. |
| 6,790,854 | B2 | 9/2004 | Tsushima et al. |

FOREIGN PATENT DOCUMENTS

| | | |
|---|---|---|
| DE | 2331223 | 1/1974 |
| DE | 41 19 767 A1 | 12/1992 |
| EP | 0 293 078 A1 | 11/1988 |
| EP | 0 447 324 A1 | 9/1991 |
| EP | 0 778 277 A1 | 6/1997 |
| EP | 1 069 124 B1 | 1/2001 |
| EP | 1 122 257 A1 | 8/2001 |
| GB | 2359079 A | 8/2001 |
| JP | 51-88994 | 8/1976 |
| WO | WO 97/40035 | 10/1997 |
| WO | WO 98/08847 | 3/1998 |
| WO | WO 98/25617 | 6/1998 |

(Continued)

OTHER PUBLICATIONS

Ahmed et al., "Novel synthesis of 1–aryl–9–alkyl–2,3,3a, 4,9,9a–hexahydro–1H–pyrrolo[2,3–b]quinoxalines by lithium aluminum hydride reduction of N–phenyl–1–benzimidazolylsuccinimides", CAPLUS 79:92106 (1973).

Chemical Abstracts, vol. 54, No. 10, May 1960, Abstract No. 9933f, C. Wayne Noell and Roland K. Robins, "Potential Purine Antagonists XVII. Synthesis of 2–methyl and 2–methylthio–6, 8–disubstituted purines", see formula III when R–SMe, Rl=Cl, R2–32 OH.

Cohen et al., "Cytokine function: A study in biologic diversity", CAPLUS 125:31527 (1996).

Cowley et al., "Preparation of 1–(3–phenyloxypropyl)piperdine derivatives as opioid receptor ligands", CAPLUS 138:39189 (2002).

Finke et al., "Preparation of piperidinylmethylcyclopentanes as modulators of CCR–5 and/or CCR–3 chemokine receptors", CAPLUS 134:56576 (2000) CAS Listing, 77 answers.

Fukuda et al., "Preparation of benzotriazole derivatives as cardiovascular agents and antipsychotics", CAPLUS 123:340149 (1995).

Gewald et al., "New Synthesis of Substituted 4–Amino–quinazolines and Their Heteroanaloga", *J. prakt. Chem.* 338:206–213 (1996).

(Continued)

*Primary Examiner*—Brian Davis
(74) *Attorney, Agent, or Firm*—Fish & Richardson P.C.

(57) ABSTRACT

The invention provides certain thiazolopyrimidine compounds of formula (I) or a pharmaceutically acceptable salt or solvate thereof: in which: A is a group of formula (a) or (b): processes and intermediates used in their preparation, pharmaceutical compositions containing them and their use in therapy

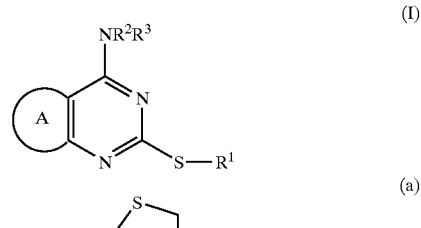

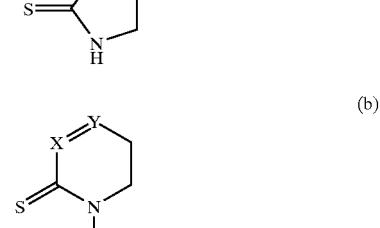

18 Claims, No Drawings

FOREIGN PATENT DOCUMENTS

| | | |
|---|---|---|
| WO | WO 99/04794 | 2/1999 |
| WO | WO 99/17773 | 4/1999 |
| WO | WO 99/36421 | 7/1999 |
| WO | WO 99/51608 | 10/1999 |
| WO | WO 00/08013 | 2/2000 |
| WO | WO 00/09511 | 2/2000 |
| WO | WO 00/38680 | 7/2000 |
| WO | WO 00/39129 | 7/2000 |
| WO | WO 00/45800 | 8/2000 |
| WO | WO 00/59502 | 10/2000 |
| WO | WO 00/76514 | 12/2000 |
| WO | WO 01/19825 | 3/2001 |
| WO | WO 01/25200 | 4/2001 |
| WO | WO 01/25242 | 4/2001 |
| WO | WO 01/58902 | 8/2001 |
| WO | WO 01/58906 | 8/2001 |
| WO | WO 01/58907 | 8/2001 |
| WO | WO 01/62758 | 8/2001 |
| WO | WO 03/024966 | 3/2003 |

OTHER PUBLICATIONS

Grant, "University of Minnesota—Twin Cities Campus College of Pharmacy, Annual Report", [online] 1999, [retrieve on Feb. 13, 2003]. Retrieved from the Internet, http://www.msi.umn.edu/general/Reports/ar99/departments/pharmacy.html.

Kiriasis et al., "Synthesis and Properties of New Pteridine Nucleosides", *Dev. Biochem.* 4:49–53 (1978).

McNaught et al., "IUPAC Compendium of Chemical Terminology, $2^{nd}$ Ed" (1997).

Ott et al., "4–amino–7, 8–dihydro–2–(methylmercapto)–8–β, –D–ribofuranosylpteridin–7–One. Modified fusion Reaction with Trimethylsilylated Pteridine Derivatives", *Nucl. Acid. Chem.* 2:735–739 (1978).

Ott et al., "Zur Synthese des 4–Amino–7–oxo–7, 8–dihydropteridin–N–8–β–D–ribofuranosids—ein strukturanaloges Nucleosid des Adenosins", *Chem.Ber.* 107:339–361 (1974).

Patent Abstracts of Japan, abstract of JP–5–202047 A (Chugai Pharmaceut. Co. Ltd.) Aug. 10, 1993.

Sato et al., "Psychotropic agents. 3. 4–(4–Substituted piperidinyl)–1–(4–flurophenyl)–1–butanones with potent neuroleptic activity", CAPLUS 89:208915 (1978).

Sato et al., "Psychotropic Agents. $3.^1$ 4–(4–Substituted piperidinyl)–1–(4–flurophenyl)–1–butanones with Potent Neuroleptic Activity," *Journal of Medicinal Chemistry* 21(11):1116–1120 (1978).

Taylor.et al., "Molecular Determinants for Recognition of RU 24969 Analogs at Central 5–Hydroxytryptamine Recognition Sites: Use of a Bilinear Function and Substituent Volumes to Describe Steric Fit," *Molecular Pharmacology* 32:42–53 (1988).

Teranishi et al., "Piperdine derivatives and pharmaceutical compositions containing them", CAPLUS 995:132947 (1981).

Trivedi et al., *Annual Reports in Medicinal Chemistry* 35:191–200 (2000).

Vandenberk et al., "1–(Benzazolylalkyl)piperidines and their salts with acids", CAPLUS 87:23274 (1977).

Vartanyan et al., "Synthesis and biological activity of 1–substituted benzimidazole and benztriazole derivatives", CAPLUS 98:4503 (1983).

West, "Solid State Chemistry and its applications", pp. 358, 365 (1988).

THIAZOLOPYTIMIDINES AND THEIR USE AS MODULATORS OF CHEMOKINE RECEPTOR ACTIVITY

This application is a 371 of PCT/SE02/00731 filed Apr. 12, 2002.

The present invention relates to certain heterocyclic compounds, processes and intermediates used in their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. At the present time, the chemokine superfamily comprises three groups exhibiting characteristic structural motifs, the Cys-X-Cys (C-X-C), Cys-Cys (C-C)) and Cys-$X_3$-Cys (C-$X_3$-C) families. The C-X-C and C-C families have sequence similarity and are distinguished from one another on the basis of a single amino acid insertion between the NH-proximal pair of cysteine residues. The C-$X_3$-C family is distinguished from the other two families on the basis of having a triple amino acid insertion between the NH-proximal pair of cysteine residues.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils. Examples include human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

The C-$X_3$-C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and CX$_3$CR1 for the C-$X_3$-C family. These receptors represent good targets for drug development since agents which modulate these receptors would be useful in the treatment of disorders and diseases such as those mentioned above.

The present invention therefore provides compounds of formula (1) and pharmaceutically acceptable salts or solvates thereof:

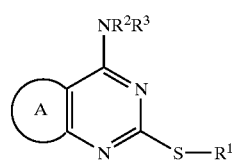

(I)

in which:
A is a group of formula (a) or (b):

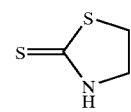

(a)

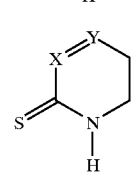

(b)

$R^1$ represents a $C_3$–$C_7$ carbocyclic, $C_1$–$C_8$ alkyl, $C_2$–$C_6$ alkenyl or $C_2$–$C_6$ alkynyl group, each of which may be optionally substituted by one or more substituent groups independently selected from halogen atoms, —$OR^4$, —$NR^5R^6$, —$CONR^5R^6$, —$COOR^7$, —$NR^8COR^9$, —$SR^{10}$; —$SO_2R^{10}$, —$SO_2NR^5R^6$, —$NR^8SO_2R^9$, an aryl or heteroaryl group, which last two may themselves be optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$–$C_6$ alkyl or trifluoromethyl groups;

$R^2$ and $R^3$ each independently represent a hydrogen atom, or a $C_3$–$C_7$ carbocyclic, $C_1$–$C_8$ alkyl, $C_2$–$C_6$ alkenyl or $C_2$–$C_6$ alkynyl group, the latter four groups may be optionally substituted by one or more substituent groups independently selected from:
(a) halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$;
(b) a 3–8 membered ring optionally containing one or more atoms selected from O, S, $NR^8$ and itself optionally substituted by $C_1$–$C_3$-alkyl or halogen; or
(c) an aryl group or heteroaryl group each of which may be optionally substituted by one or more substituents independently selected from halogen atoms, cyano, nitro, —$OR^4$, —$NR^5R^6$, —$CONR^5R^6$, —$NR^8COR^9$, —$SO_2NR^5R^6$, —$NR^8SO_2R^9$, $C_1$–$C_6$ alkyl and trifluoromethyl groups;

$R^4$ represents hydrogen, $C_1$–$C_6$ alkyl or a phenyl group the latter two of which may be optionally substituted by one or more substituent groups independently selected from halogen atoms, phenyl, —$OR^{11}$ and —$NR^{12}R^{13}$ $R^5$ and $R^6$ independently represent a hydrogen atom or a $C_1$–$C_6$ alkyl or phenyl group the latter two of which may be optionally substituted by one or more substituent groups independently selected from halogen atoms, phenyl, —$OR^{14}$ and —$NR^{15}R^{16}$, —$CONR^{15}R^{16}$, —$NR^{15}COR^{16}$, —$SONR^{15}R^{16}$, $NR^{15}SO_2R^{16}$ or $R^5$ and $R^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —$OR^{14}$, —$COOR^{14}$, —$NR^{15}R^{16}$, —$CONR^{15}R^{16}$, —$NR^{15}COR^{16}$, —$SONR^{15}R^{16}$, $NR^{15}SO_2R^{16}$ or $C_1$–$C_6$ alkyl, itself optionally substituted by one or more substituents independently selected from halogen atoms and —$NR^{15}R^{16}$ and —$OR^{17}$ groups;

$R^{10}$ represents a $C_1$–$C_6$-alkyl or a phenyl group, either of which may be optionally substituted by one or more substituent groups independently selected from halogen atoms, phenyl, —OR$^{17}$ and —NR$^{15}$R$^{16}$, X is CH or CCN, Y is N or CR$^{18}$, and each of R$^7$, R$^8$, R$^9$, R$^{11}$, R$^{12}$, R$^{13}$, R$^{14}$ R$^{15}$, R$^{16}$, R$^{17}$ and R$^{18}$ independently represents a hydrogen atom or a C$_1$–C$_6$, alkyl, or a phenyl group.

In the context of the present specification, unless otherwise indicated, an alkyl or alkenyl group or an alkyl or alkenyl moiety in a substituent group may be linear or branched.

Aryl groups include phenyl and naphthyl. Heteroaryl is defined as a 5- or 6-membered aromatic ring optionally containing one or more heteroatoms selected from N, S, O. Examples include pyridine, pyrimidine, thiazole, oxazole, pyrazole, imidazole, furan.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Suitably the group R$^1$ represents a C$_3$–C$_7$ carbocyclic, C$_1$–C$_8$ alkyl, C$_2$–C$_6$ alkenyl or C$_2$–C$_6$ alkynyl group, each of which may be may be optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, an aryl or heteroaryl group both of which can be optionally substituted by one or more substituents independently selected from halogen atoms, cyano, nitro, —OR$^4$, —NR$^5$R$^6$, —CONR$^5$R$^6$, —COOR$^7$, —NR$^8$COR$^{10}$, —SR$^{10}$, —SO$_2$R$^{10}$, —SO$_2$NR$^5$R$^6$, —NR$^8$SO$_2$R$^{10}$, C$_1$–C$_6$ alkyl or trifluoromethyl groups. Particularly advantageous compounds of formula (I) are those in which R$^1$ represents an optionally substituted benzyl group. More preferably R$^1$ represents benzyl or benzyl substituted by one or more C$_1$–C$_6$ alkyl, C$_1$–C$_6$ alkoxy, or halogen atoms, in particular benzyl substituted by two fluoro atoms.

Preferably one of R$^2$ and R$^3$ is hydrogen and the other is C$_1$–C$_8$ alkyl substituted by hydroxy and one or more methyl or ethyl groups. More preferably one of R$^2$ and R$^3$ is hydrogen and the other is CH(CH$_3$)CH$_2$OH, CH(Et)CH$_2$OH, C(CH$_3$)$_2$CH$_2$OH or CH(CH$_2$OH)$_2$. When one of R$^2$ and R$^3$ is hydrogen and the other is CH(CH$_3$)CH$_2$OH or CH(Et)CH$_2$OH the resulting compounds of formula (I) are preferably in the form of the (R) isomer. Most preferably one of R$^2$ and R$^3$ is hydrogen and the other is CH(CH$_3$)CH$_2$OH.

Suitably in formula (b) X represents CH or CCN and Y is N or CR$^{18}$. Preferably X is CH and Y is N.

Particularly preferred compounds of the invention include:

5-[[(2,3-difluorophenyl)methyl]thio]-7-[[(1R)-2-hydroxy-1-methylethyl]amino]-thiazolo[4,5-d]pyrimidine-2(3H)-thione, 2-[[(2,3-difluorophenyl)methyl]thio]4-[[(1R)-2-hydroxy-1-methylethyl]amino]-7(8H)-pteridinethione, and pharmaceutically acceptable salts thereof.

According to the invention there is also provided a process for the preparation of a compound of formula (I) which comprises:

(a) treatment of a compound of formula (IIA):

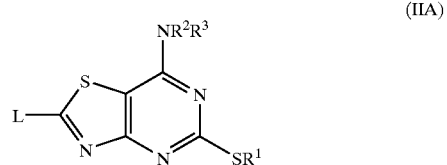

(IIA)

where R$^1$, R$^2$ and R$^3$ are as defined in formula (I) or are protected derivatives thereof and L is a leaving group with a metal hydrosulphide, or (b) treatment of a compound of formula (IIB):

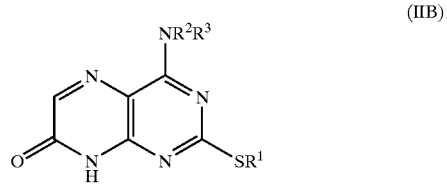

(IIB)

where R$^1$, R$^2$ and R$^3$ are as defined in formula (I) or are protected derivatives thereof with a thiating agent, and optionally thereafter process (a) or (b) and in any order:

removing any protecting groups forming a pharmaceutically acceptable salt.

The reaction of compounds of formula (IIA) with a metal hydrosulphide may be carried out in a solvent such as DMSO at a temperature between 0° C. and 100° C. Suitable leaving groups L include halogen, especially chloro or bromo, and a suitable metal hydrosulphide is sodium hydrosuphide.

The reaction of compounds (IIB) with a thiating agent may be carried out in a solvent such as dioxan at reflux. A suitable thiating agent is Lawesson's reagent.

Compounds of formula (IIA) where R$^1$, R$^2$ and R$^3$ are as defined in formula (I) and L is a leaving group may be prepared from compounds of formula (IIA) where R$^1$, R$^2$ and R$^3$ are as defined above and L is NH$_2$ by treatment with sodium nitrite and aqueous mineral acid at a temperature between 0° C. and room temperature. Suitable acids include hydrochloric acid.

Compounds of formula (IIA) where R$^1$, R$^2$ and R$^3$ are as defined in formula (I) and L is NH$_2$ may be prepared by treatment of a compound of formula (III):

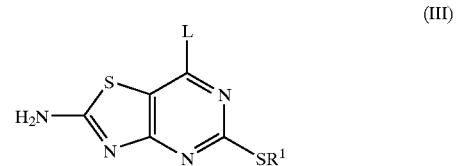

(III)

where R$^1$ is as defined in formula (I) and L is a leaving group such as chlorine with an amine HNR$^2$R$^3$ where R$^2$ and R$^3$ are as defined in formula (I). The reaction may be carried out in a solvent such as N-methyl-pyrrolidine at a temperature between 0° C. and 150° C.

Compounds of formula (III) where R$^1$ is as defined in formula (I) and L is a halogen may be prepared by treating a compound of formula (III) where R$^1$ is as defined in formula (I) and L is a hydroxyl group with a halogenating agent such as phosphorous oxychloride. The reaction may be carried out in the presence of dimethylaniline at reflux.

Compounds of formula (I) where $R^1$ is as defined in formula (I) and L is a hydroxyl group may be formed by treatment of a compound of formula (IV) with a compound of formula $R^1X$ where $R^1$ is as defined above and X is a leaving group such as bromide in the presence of a base such as potassium tert-butoxide in an inert solvent such as DMSO at ambient temperature.

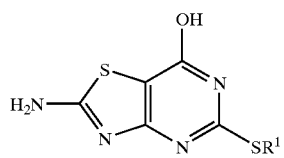

(IV)

Compounds of formula (IIB) where $R^1$, $R^2$ and $R^3$ are as defined in formula (I) may be prepared by treatment of a compound of formula (V):

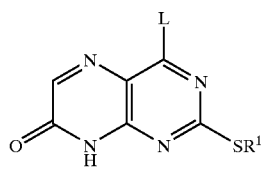

(V)

where $R^1$ is as defined in formula (I) and L is a leaving group such as bromo with an amine $HNR^2R^3$ where $R^2$ and $R^3$ are as defined in formula (I). The reaction may be carried out in a solvent such as N-methyl-pyrrolidine at a temperature between 0° C. and 150° C.

Compounds of formula (V) where $R^1$ is as defined in formula (I) and L is a leaving group such as bromo may be prepared by treating a compound of formula (V) where $R^1$ is as defined above and L is $NH_2$ with a diazotizing agent such as isoamyl nitrite in the presence of a halogenating agent such as bromoform. The reaction may be performed in a solvent such as DMSO at a temperature between 0° C. and 150° C.

Compounds of formula (V) where $R^1$ is as defined in formula (I) and L is $NH_2$ may be prepared by treatment of a compound of formula (VI):

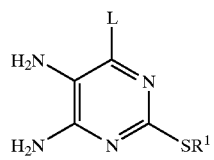

(VI)

where $R^1$ and L are as defined above with ethyl glyoxylate in the presence of a base such as sodium methoxide in a solvent such as methanol at room temperature.

Compounds of formula (VI) where $R^1$ is as defined in formula (I) and L is $NH_2$ may be prepared by treating a compound of formula (VII) where $R^1$ and L are as defined above with a reducing agent such as sodium hydrosulphite.

The reaction may be carried out in a solvent such as water at reflux.

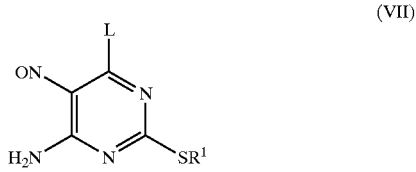

(VII)

Compounds of formula (VII) where $R^1$ is as defined in formula (I) and L is $NH_2$ may be prepared by treating a compound of formula (VIII) where $R^1$ and L are as defined above with a nitrosating agent such as sodium nitrite. The reaction may be performed in a solvent such as aqueous acetic acid at a temperature between 0° C. and 100° C.

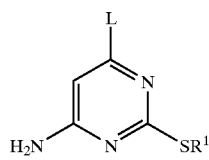

(VIII)

Compounds of formula (VIII) where $R^1$ is as defined in formula (I) and L is $NH_2$ may be prepared by treating a compound of formula (IX) with a compound of formula $R^1X$ where $R^1$ is as defined above and X is a leaving group such as bromide in the presence of a base such as potassium tert-butoxide. The reaction may be performed in a solvent such as DMSO at room temperature.

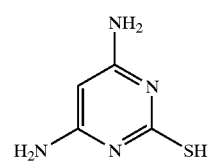

(IX)

Compounds of formula (IV) or (IX) are either commercially available or are well known in the literature.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

The compounds of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

The compounds of formula (I) have activity as pharmaceuticals, in particular as modulators of chemokine receptor (especially CXCR2) activity, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barre syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal diorders, e.g. tropical spastic paraparesis, and stiff-man syndrome: paraneoplastic syndromes, e.g. cerebellar degeneration and encephalomyelitis; CNS trauma; migraine; and stroke.

(6) (other tissues and systemic disease) atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) (allograft rejection) acute and chronic following, for example, transplantation of kidney, heart, liver, lung, bone marrow, skin and cornea; and chronic graft versus host disease;

(8) Cancers, especially non-small cell lung cancer (NSCLC), malignant melanoma, prostate cancer and squamous sarcoma, and tumour metastasis;

(9) Diseases in which angiogenesis is associated with raised CXCR2 chemokine levels (e.g. NSCLC, diabetic retinopathy).

(10) Cystic fibrosis, re-perfusion injury in the heart, brain, peripheral limbs and other organs.

(11) Burn wounds & chronic skin ulcers

(12) Reproductive Diseases (e.g. Disorders of ovulation, menstruation and implantation, Pre-term labour, Endometriosis)

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CXC chemokine receptor subfamily, more preferably the target chemokine receptor is the CXCR2 receptor, Particular conditions which can be treated with the compounds of the invention are psoriasis, rheumatoid arthritis and diseases in which angiogenesis is associated with raised CXCR2 chemokine levels, and COPD. It is preferred that the compounds of the invention are used to treat rheumatoid arthritis.

As a further aspect of the present invention, certain compounds of formula (I) may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula (I), or a pharmaceutically acceptable salt or solvate thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compounds of the invention are administered orally.

The invention will now be further illustrated by reference to the following examples. In the examples the Nuclear Magnetic Resonance (NMR) spectra were measured on a Varian Unity Inova 300 or 400 MHz spectrometer and the Mass Spectrometry (MS) spectra measured on a Finnigan Mat SSQ7000 or Micromass Platform spectrometer. Where necessary, the reactions were performed under an inert atmosphere of either nitrogen or argon. Chromatography was generally performed using Matrex Silica 60® (35–70 micron) or Prolabo Silica gel 60® (35–70 micron) suitable for flash silica gel chromatography. High pressure liquid chromatography purification was performed using either a Waters Micromass LCZ with a Waters 600 pump controller, Waters 2487 detector and Gilson FC024 fraction collector or a Waters Delta Prep 4000. The abbreviations m.p. and DMSO used in the examples stand for melting point and dimethyl sulphoxide respectively.

EXAMPLES

Example 1

5[[(2,3-difluorophenyl)methyl]thio]-7-[[(1R)-2-hydroxy-1-methylethyl]amino]-thiazolo[4,5-d]pyrimidine-2(3H)-thione a) 2-Amino-5-[[(2,3-difluorophenyl)methyl]thio]thiazolo[4,5-d]pyrimidin-7(4H)-one Potassium t-butoxide solution (0.45 ml of 1M solution in tetrahydrofuran) was added to a stirred solution of 2-amino-5,6-dihydro-5-thioxo-thiazolo[4,5-d]pyrimidin-7(4H)-one (0.09 g) [Cited: Indian J. Chem., Sect. B (1989), 28B(11), 964–5.] and 2,3-difluorobenzyl bromide in dimethyl sulphoxide (2 ml). After stirring for 3 days, the reaction mixture was poured onto water to give the subtitled compound, isolated by filtration.

MS (APCI) 327 (M+H$^+$, 100%).

b) 7–Chloro-5-[[(2,3-difluorophenyl)methyl]thio]thiazolo[4,5-d]pyrimidin-2-amine The product from example 1, step (a) (0.89 g), phosphorus oxychloride (12 ml) and N,N-dimethylaniline (1.2 ml) were heated at reflux for 2 hours. The cooled reaction mixture was poured onto ice water and stirred for 2 hours. Chromatography (SiO$_2$, methanol/dichloromethane as eluant) gave the subtitled compound.

m.p. 217–218.5° C.

MS (APCI) 346(M+H, 100%).

(c) (2R)-2-[[(2-amino-5-[[(2,3-difluorophenyl)methyl]thio]thiazolo[4,5-d]pyrimidin-7-yl]amino]-1-propanol, The product from example 1, step (b) (70.0 g) and (R)-1-amino-propan-2-ol (32 ml) in N-methylpyrrolidinone (600 ml) and Hunigs base (71 ml) was heated at 110° C. for 16 hours. The mixture was poured into water (5 L) and the crude product collected at by filtration. This solid was purified by recrystallisation from acetonitrile (2.5 L) to give 65 g of the subtitled compound.

MS (APCI) 384 (M+H, 100%).

(d) (2R)-2-[[2-chloro-5-[[(2,3-difuorophenyl)methyl]thio]thiazolo[4,5-d]pyrimidin-7-yl]amino]-1-propanol, The product from example 1, step (c) (0.5 g) was dissolved in concentrated hydrochloric acid (18 ml). To this solution was added a mixture of acetonitile (8 ml) and water (16 ml), maintaining the temperature below 20° C. The solution was then cooled in an ice bath and a solution of sodium nitrite (0.135 g) in water (0.5 ml) added. Upon completion of addition the mixture was allowed to stir for a further 1 hour. The solid was then collected by filtration, washed well with water and dried at 40° C. in vacuo to give the subtitled compound (0.43 g).

MS (APCI) 403 (M+H, 100%).

(e) 5-[[(2,3-difluorophenyl)methyl]thio]-7-[[(1R)-2-hydroxy-1-methylethyl]amino]-thiazolo[4,5-d]pyrimidine-2(3H)-thione, A mixture of the product from example 1, step (d) (150 mg) and sodium hydrosulfide (150 mg) in DMSO (5 ml) was stirred at room temperature for 30 mins. The mixture was poured into water (100 ml) and the pH adjusted to 7 and the product collected by filtration and purified by chromatography (SiO$_2$, ethyl acetate/dichloromethane as eluant) to give the title compound (67 mg).

MS (APCI) 401 (M+H, 100%).

NMR δH (d$_6$-DMSO) 14.06 (1H, s), 7.75 (1H, d), 7.45–7.11 (3H, m), 4.75 (1H, bs), 4.41 (2H, m), 4.21 (1H, bs), 3.46–3.32 (2H, m), 1.09 (3H, d).

Example 2

2-[[(2,3-Difluorophenyl)methyl]thio]-4-[[(1R)-2-hydroxy-1-methylethyl]amino]-7(8H)-pteridinone a) 2-[[(2,3-Difluorophenyl)methyl]thio]-4,6-pyrimidinediamine 4,6-diamino-2-pyrimidinethiol (7.3 g) was dissolved in DMSO (100 ml) at room temperature under an atmosphere of nitrogen. Potassium tert-butoxide (1M in THF, 48.3 ml) was added followed by 2,3-difluorobenzyl-bromide (10.0 g). The mixture was stirred for 2 hours at room temperature. The reaction mixture was then partitioned between ethyl acetate and ammonium chloride. The organic phase was washed with ammonium chloride (3×) and brine, then dried over magnesium sulphate and evaporated to give the subtitled product as a white solid (12.2 g)

MS: ADCI (+ve) 269 (M+1)

b) 2-[[(2,3-Difluorophenyl)methyl]thio]-5-nitroso-4,6-pyrimidinediamine

The product of example 2, step (a) (2.5 g) was dissolved in acetic acid (150 ml) and the solution cooled to 5° C. A solution of sodium nitrite (625 mg) in water (50 ml) was added dropwise resulting in a dark blue colouration. The reaction was stirred at room temperature for 30 minutes during which time a pink solid precipitated from solution. This was isolated by filtration and washed with water, then dried at 50° C. to give the sub-titled product as a blue solid (4.14 g)

MS: ADCI (+ve) 298 (M+1)

$^1$H NMR: δ (DMSO) 4.44 (s, 2H), 7.13–7.54 (m, 3H), 8.13 (s, 1H), 8.51 (s, 1H), 9.10 (s, 1H), 10.18 (s, 1H).

c) 2-[[(2,3-Difluorophenyl)methyl]thio]-4,5,6-pyrimidinetriamine

To a suspension of the product of example 2, step (b) (2 g) in boiling water (40 ml) was added $Na_2S_2O_4$ (5.4 g) portion-wise. The suspension was allowed to cool and then 50% sulphuric acid was added slowly and then the mixture was cooled to 0° C. The solid was isolated by filtration and washed with cold water, then dried over $P_2O_5$ at 50° C. to give the sub-titled product as a yellow solid.

MS: ADCI (+ve) 284 (M+1)

$^1$H NMR: δ (DMSO) 4.33 (s, 2H), 6.42 (brs, 3H), 7.10–7.48 (m, 3H)

d) 4-amino-2-[[(2,3-difluorophenyl)methyl]thio]-7(8H)-pteridinone

The product of example 2, step (c) (100 mg) was dissolved in a solution of sodium (0.05 g) in methanol (5 ml). This was left to stir for 15 min at room temperature, then ethyl glyoxalate (134 μl) was added to the mixture which was left to stir for 12 hr at room temperature. Water (5 ml) was added, then concentrated hydrochloric acid was slowly .5 added to acidify the solution to ~pH5 whereupon a solid precipitated which was isolated by filtration and dried over $P_2O_5$ at 50° C. to yield a pale yellow solid (44.5 mg).

MS: ADCI (+ve) 322 (M+1).

$^1$H NMR: δ (DMSO) 4.18 (s, 2H), 7.11–7.58 (m, 3H), 7.84 (s, 1H), 12.69 (bs, 1H).

e) 4-bromo-2-[[(2,3-difluorophenyl)methyl]thio]-7(8H)-pteridinone

The product of example 2, step (d) (6.0 g) was suspended in DMSO (90 ml) and bromoform (60 ml) was added and the mixture was heated to 100° C. Isopentylnitrite (25 ml) was added and the mixture stirred for 5 min. The mixture was quickly cooled in an ice bath then evaporated to leave an oil. This was repeated three times. Acetonitrile (200 ml) was added and the solid which separated was removed by filtration. The solvent was evaporated and the residue was purified by flash chromatography, eluting with dichloromethane and then 5% ethyl acetate in dichloromethane to give a yellow solid which was slurried with ether then collected. The solid was washed with ether and dried to give the subtitled compound as a colourless solid (8.74 g).

MS: APCI (–ve) 382/4 (M–H), 382 (100%)

$^1$H NMR: δ (DMSO) 4.47 (s, 2H), 7.13–7.55 (m, 3H), 8.14 (s, 1H), 13.33 (bs, 1H).

f) 2-[[(2,3-difluorophenyl)methyl]thio]-4-[[(1R)-2-hydroxy-1-methylethy]amino]-7(8H)-pteridinone The product of example 2, step (e) (8.7 g) was dissolved in N-methylpyrrolidinone (40 ml) and Hunigs base (7.9 ml) was added followed by D-alaninol (2.7 ml). The mixture was stirred at 100° C. for 15 mins. The cooled solution was poured onto water, (1l), and acidified with dilute hydrochloric acid. The solid which separated was collected, washed with water and air dried. Crystallisation from acetonitrile afforded the title compound as a pale yellow solid (7.4 g).

m.p. 215–217° C.

MS: APCI (+ve) 380 (M+H, 100%)

$^1$H NMR: δ (DMSO) 1.14 (d, 3H), 3.48 (m, 2H), 4.31 (m, 1H), 4.45 (dd, 2H) 4.82 (t, 1H), 7.15 (m, 1H), 7.33 (m, 1H), 7.47 (t, 1H), 7.76 (d, 1H), 7.83 (d, 1H), 12.70 (s, 1H).

g) 2-[[(2,3-Difluorophenyl)methyl]thio-4-[[(1R)-2-hydroxy-1-methylethyl]amino-7(8H)-pteridinethione The product of example 2, step (f) (0.50 g) and Lawessons reagent (1.06 g) were stirred in dioxan (10 mL) and heated under reflux for 30 mins. Water (5 mL) was added and heating continued for 10 mins. The cooled mixture was diluted with water to give a suspension. The solid was collected, washed with water and dried. Purification by flash chromatography over silica using dichloromethane/acetonitrile (5–10%) as eluant afforded the title compound 0.225 g.

mp 232–233° C.

MS: APCI 396 (M+H, 100%)

$^1$H NMR: δ (DMSO) 1.15(d, 3H), 3.47 (m, 2H), 4.30 (m, 1H), 4.46 (q, 2H), 4.82 (bm, 1H), 7.16 (m, 1H), 7.34 (m, 1H), 7.53 (t, 1H), 8.10 (d, 1H), 8.21 (s, 1H), 14.45 (s, 1H).

Pharmacological Data

Ligand Binding Assay

[$^{125}$I]IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp 16283–16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 μg/ml soybean trypsin inhibitor, 3 mM benzamidine, 0.5 μg/ml leupeptin and 100 μg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at –70° C. in homogenisation buffer supplemented with Tyrode's salt solution (137 mM NaCl, 2.7 mM KCl, 0.4 mM $NaH_2PO_4$), 0.1% (w/v) gelatin and 10% (v/v) glycerol.

All assays were performed in a 96-well MultiScreen 0.45 μm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM $CaCl_2$, 1 mM $MgCl_2$, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compounds of formula (I) according to the Examples were found to have $IC_{50}$ values of less than (<) 10 μM.

Intracellular Calcium Mobilisation Assay

Human neutrophils were prepared from EDTA-treated peripheral blood, as previously described (Baly et al. (1997)

Methods in Enzymology 287 pp 70–72), in storage buffer [Tyrode's salt solution (137 mM NaCl, 2.7 mM KCl, 0.4 mM $NaH_2PO_4$) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp 513–519). Cells were loaded for 1 hour at 37° C. in loading buffer (storage buffer with 0.1% (w/v) gelatin) containing 5 μM fluo-3 AM ester, washed with loading buffer and then resuspended in Tyrode's salt solution supplemented with 5.7 mM glucose, 0.1% (w/v) bovine serum albumin (BSA), 1.8 mM $CaCl_2$ and 1 mM $MgCl_2$. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an $A_{50}$ concentration of GROα and the transient increase in fluo-3 fluorescence ($\lambda_{Ex}$=490 nm and $\lambda_{Em}$=520 nm) monitored using a FLIPR (Fluorometric Imaging Plate Reader, Molecular Devices, Sunnyvale, U.S.A.).

The compounds of formula (I) according to the Examples were tested and found to be antagonists of the CXCR2 receptor in human neutrophils.

What is claimed is:

1. A compound of formula (I) or a pharmaceutically acceptable salt or solvate thereof:

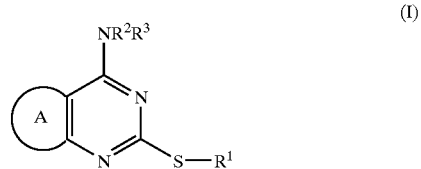

(I)

in which:

A is a group of formula (a) or (b):

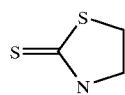

(a)

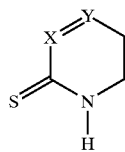

(b)

$R^1$ represents a $C_3$–$C_7$ carbocyclic, $C_1$–$C_8$ alkyl, $C_2$–$C_6$ alkenyl or $C_2$–$C_6$ alkynyl group, each of which may be optionally substituted by one or more substituent groups independently selected from halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, an aryl or heteroaryl group, which last two may themselves be optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$–$C_6$ alkyl or trifluoromethyl groups;

$R^2$ and $R^3$ each independently represent a hydrogen atom, or a $C_3$–$C_7$ carbocyclic, $C_1$–$C_8$ alkyl, $C_2$–$C_6$ alkenyl or $C_2$–$C_6$ alkynyl group, the latter four groups may be optionally substituted by one or more substituent groups independently selected from:

(a) halogen atoms, —$OR^4$, —$NR^5R^6$—$CONR^5R^6$, —$COOR^7$, —$NR^8COR^9$, —$SR^{10}$, —$SO_2R^{10}$, —$SO_2NR^5R^6$, —$NR^8SO_2R^9$;

(b) a 3–8 membered ring optionally containing one or more atoms selected from O, S, $NR^8$ and itself optionally substituted by $C_1$–$C_3$-alkyl or halogen; or (c) an aryl group or heteroaryl group each of which may be optionally substituted by one or more substituents independently selected from halogen atoms, cyano, nitro, —$OR^4$, —$NR^5R^6$, —$CONR^5R^6$, —$NR^8COR^9$, —$SO_2NR^5R^6$, —$NR^8SO_2R^9$, $C_1$–$C_6$ alkyl and trifluoromethyl groups;

$R^4$ represents hydrogen, $C_1$–$C_6$ alkyl or a phenyl group the latter two of which may be optionally substituted by one or more substituent groups independently selected from halogen atoms, phenyl, —$OR^{11}$ and —$NR^{12}R^{13}$;

$R^5$ and $R^6$ independently represent a hydrogen atom or a $C_1$–$C_6$ alkyl or phenyl group the latter two of which may be optionally substituted by one or more substituent groups independently selected from halogen atoms, phenyl, —$OR^{14}$ and —$NR^{15}R^{16}$, —$CONR^{15}R^{16}$, —$NR^{15}COR^{16}$, —$SONR^{15}R^{16}$, $NR^{15}SO_2R^{16}$; or $R^5$ and $R^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —$OR^{14}$, —$COOR^{14}$, —$NR^{15}R^{16}$, —$CONR^{15}R^{16}$, —$NR^{15}COR^{16}$, —$SONR^{15}R^{16}$, $NR^{15}SO_2R^{16}$ or $C_1$–$C_6$ alkyl, itself optionally substituted by one or more substituents independently selected from halogen atoms and —$NR^{15}R^{16}$ and —$OR^{17}$ groups;

$R^{10}$ represents a $C_1$–$C_6$-alkyl or a phenyl group, either of which may be optionally substituted by one or more substituent groups independently selected from halogen atoms, phenyl, —$OR^{17}$ and —$NR^{15}R^{16}$, X is CH or CCN, Y is N or $CR^{18}$, and each of $R^7$, $R^8$, $R^9$, $R^{11}$, $R^{12}$, $R^{13}$, $R^{14}$ $R^{15}$, $R^{16}$, $R^{17}$ and $R^{18}$ independently represents a hydrogen atom or a $C_1$–$C_6$, alkyl, or a phenyl group.

2. A compound according to claim 1, wherein $R^1$ represents an optionally substituted benzyl group.

3. A compound according to claim 1, wherein one of $R^2$ and $R^3$ is hydrogen and the other is $C_1$–$C_8$ alkyl substituted by hydroxy and one or more methyl or ethyl groups.

4. A compound according to claim 1 in which A is a group of formula (a).

5. A compound according to claim 1 in which A is a group of formula (b).

6. A compound according to claim 5 in which X is CH and Y is N.

7. A compound according to claim 1 selected from:

-[[(2,3-difluorophenyl)methyl]thio]-7-[[(1R)-2-hydroxy-1-methylethyl]amino]-thiazolo[4,5-d]pyrimidine-2 (3H)-thione, 2-[[(2,3-difluorophenyl)methyl]thio]-4-[[(1R)-2-hydroxy-1-methylethyl]amino]-7(8H)-pteridinethione, and pharmaceutically acceptable salts thereof.

8. A pharmaceutical composition comprising a compound of formula (I), or a pharmaceutically acceptable salt or solvate thereof, as claimed in claim 1 in association with a pharmaceutically acceptable adjuvant, diluent or carrier.

9. A method of treating a chemokine mediated disease wherein the chemokine binds to one or more chemokine receptors, which comprises administering to a patient a therapeutically effective amount of a compound of formula (I), or a pharmaceutically acceptable salt or solvate thereof, as claimed in claim 1.

10. A method according to claim 9 in which the chemokine receptor belongs to the CXC chemokine receptor subfamily.

11. A method according to claim 9 in which the chemokine receptor is the CXCR2 receptor.

12. A method of treating an inflammatory disease in a patient suffering from, or at risk of, said disease, which comprises administering to the patient a therapeutically effective amount of a compound of formula (I), or a pharmaceutically acceptable salt or solvate thereof, as claimed in claim 1.

13. A method according to claim 12, wherein the disease is psoriasis, rheumatoid arthritis or COPD.

14. A method according to claim 12, wherein the disease is rheumatoid arthritis.

15. A process for the preparation of a pharmaceutical composition as claimed in claim 8, which comprises mixing a compound of formula (I) or a pharmaceutically acceptable salt or solvate thereof:

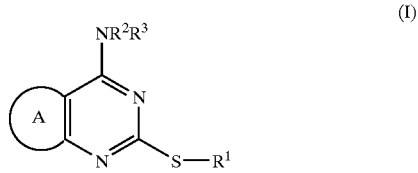

(I)

in which:

A is a group of formula (a) or (b):

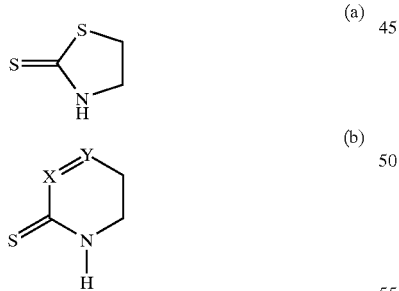

$R^1$ represents a $C_3$–$C_7$ carbocyclic, $C_1$–$C_8$ alkyl, $C_2$–$C_6$ alkenyl or $C_2$–$C_6$ alkynyl group, each of which may be optionally substituted by one or more substituent groups independently selected from halogen atoms, —$OR^4$, —$NR^5R^6$, —$CONR^5R^6$, —$COOR^7$, —$NR^8COR^9$, —$SR^{10}$, —$SO^2R^{10}$, —$SO^2NR^5R^6$, —$NR^8SO_2R^9$, an aryl or heteroaryl group which last two may themselves be optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$–$C_6$ alkyl or trifluoromethyl groups;

$R^2$ and $R^3$ each independently represent a hydrogen atom, or a $C_3$–$C_7$ carbocyclic, $C_1$–$C_8$ alkyl, $C_2$–$C_6$ alkenyl or $C_2$–$C_6$ alkynyl group, the latter four groups may be optionally substituted by one or more substituent groups independently selected from:

(a) halogen atoms, —$OR^4$, —$NR^5R^6$—$CONR^5R^6$, —$COOR^7$, —$NR^8COR^9$, —$SR^{10}$, —$SO_2R^{10}$, —$SO_2NR^5R^6$, —$NR^8SO_2R^9$;

(b) a 3–8 membered ring optionally containing one or more atoms selected from O, S, $NR^8$ and itself optionally substituted by $C_1$–$C_3$-alkyl or halogen; or (c) an aryl group or heteroaryl group each of which may be optionally substituted by one or more substituents independently selected from halogen atoms, cyano, nitro, —$OR_4$, —$NR^5R^6$, —$CONR^5R^6$, —$NR^8COR^9$, —$SO_2NR^5R^6$, —$NR^8SO_2R^9$, $C_1$–$C_6$ alkyl and trifluoromethyl groups;

$R^4$ represents hydrogen, $C_1$–$C_6$ alkyl or a phenyl group the latter two of which may be optionally substituted by one or more substituent groups independently selected from halogen atoms, phenyl, —$OR^{11}$ and —$NR^{12}R^{13}$;

$R^5$ and $R^6$ independently represent a hydrogen atom or a $C_1$–$C_6$ alkyl or phenyl group the latter two of which may be optionally substituted by one or more substituent groups independently selected from halogen atoms, phenyl, —$OR^{14}$ and —$NR^{15}R^{16}$, —$CONR^{15}R^{16}$, —$NR^{15}COR^{16}$, —$SONR^{15}R^{16}$, $NR^{15}SO_2R^{16}$; or $R^5$ and $R^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —$OR^{14}$, —$COOR^{14}$, —$NR^{15}R^{16}$, —$CONR^{15}R^{16}$, —$NR^{15}COR^{16}$, —$SONR^{15}R^{16}$, $NR^{15}SO_2R^{16}$ or $C_1$–$C_{16}$ alkyl, itself optionally substituted by one or more substituents independently selected from halogen atoms and —$NR^{15}R^{16}$ and —$OR^{17}$ groups;

$R^{10}$ represents a $C_1$–$C_6$-alkyl or a phenyl group, either of which may be optionally substituted by one or more substituent groups independently selected from halogen atoms, phenyl, —$OR^{17}$ and —$NR^{15}R^{16}$, X is CH or CCN, Y is N or $CR^{18}$, and each of $R^7$, $R^8$, $R^9$, $R^{11}$, $R^{12}$, $R^{13}$, $R^{14}$ $R^{15}$, $R^{16}$, $R^{17}$ and $R^{18}$ independently represents a hydrogen atom or a $C_1$–$C_6$, alkyl, or a phenyl group, with a pharmaceutically acceptable adjuvant, diluent or carrier.

16. A method according to claim 12, wherein A is a group of formula (a) in the compound of formula I.

17. A method according to claim 12, wherein A is a group of formula (b) in the compound of formula I.

18. A method according to claim 12, wherein the compound of formula I is selected from -[[(2,3-difluorophenyl)methyl]thio]-7-[[(1R)-2-hydroxy-1-methylethyl]amino]-thiazolo[4,5-d]pyrimidine-2(3H)-thione, 2-[[(2,3-difluorophenyl)methyl]thio]-4-[[(1R)-2-hydroxy-1-methylethyl]amino]-7(8H)-pteridinethione, and pharmaceutically acceptable salts thereof.

* * * * *